US00PP11110P

United States Patent [19]

Jamieson et al.

[11] Patent Number: Plant 11,110

[45] Date of Patent: Oct. 26, 1999

[54] STRAWBERRY PLANT NAMED 'CAVENDISH'

[75] Inventors: Andrew R. Jamieson, Kentville; Nancy L. Nickerson, Port Williams; Katherine A. Sanford, Centreville, all of Canada

[73] Assignee: Agriculture Canada, Kentville, Canada

[21] Appl. No.: 08/535,610

[22] Filed: Sep. 8, 1995

Related U.S. Application Data

[63] Continuation of application No. 08/263,391, Jun. 20, 1994, abandoned, which is a continuation of application No. 08/056,865, Apr. 20, 1993, abandoned, which is a continuation of application No. 07/815,987, Jan. 2, 1992, abandoned.

[51] Int. Cl.[6] ..... A01H 5/00

[52] U.S. Cl. ..... Plt./208

[58] Field of Search ..... Plt./48, 208, 209

[56] References Cited

PUBLICATIONS

Jamieson et al, *HortScience*, 26:1561–1563 (1991) is the scientific publication naming and making available 'Cavendish'.

Agriculture Canada, Kentville Research Station Information Release No. 13, Jan. 22, 1990, describes the cultivar "to be related" in the future.

Agriculture Canada, Kentville Research Station Information Release No. 14, Feb. 2, 1990, describes the cultivar "to be released" in the future.

*Primary Examiner*—Howard J. Locker

[57] ABSTRACT

A new and distinct variety of strawberry (*Fragaria*× *ananassa* Duchesne) offers strawberry growers of the Northeast climatic zone a cultivar that is high yielding and resistant to red stele, producing large fruit of good quality in the midseason. The strawberry is named 'Cavendish' and was tested as K83-4.

2 Drawing Sheets

CROSS-REFERENCE TO RELATED APPLICATIONS

This application is a continuation of plant application Ser. No. 08/263,391, filed Jun. 20, 1994, now abandoned, which is a continuation of plant application Ser. No. 08/056,865, filed Apr. 20, 1993, now abandoned, which is a continuation of plant application Ser. No. 07/815,987, filed Jan. 2, 1992, now abandoned.

BACKGROUND OF THE INVENTION

'Cavendish' strawberry (*Fragaria*×*ananassa* Duchesne) offers strawberry growers of the Northeast climatic zone (Himelrick and Galletta, (ed) "Small Fruit Crop Management" Prentice Hall, Englewood Cliff, N.J., 1990, pp. 14–82) a cultivar that is high yielding and resistant to red stele, producing large fruit of good quality in the midseason. Breeding for resistance to red stele root rot (caused by *Phytophthora fragariae* Hickman) began at Kentville in 1969, after Gourley and Craig (Can. Plant Dis. Surv. 48:93–94, 1968) demonstrated the field resistance of 'Guardsman'. Significant progress was not made until 'Earliglow' was included in the crossing program in 1977, and the sand bench screening method (Scott et al., *HortSci* - 11:257–258, 1976) was adopted in 1978. The 'Earliglow' derivatives 'Annapolis' and 'Cornwallis', released in 1984, provided immediate relief for those growers with soils infested in *P. fragariae*. These two early-midseason cultivars have achieved only moderate yields when compared to the midseason cultivars 'Kent' and 'Cavendish'.

'Cavendish' is named after the most popular tourist location of Price Edward Island.

Origin

'Cavendish', tested as K83-4, is a seedling from a 'Glooscap'×'Annapolis' cross made under the direction of D. L. Craig in 1981 at Kentville, Nova Scotia.

The seed parent of 'Cavendish' was 'Glooscap' which is a hybrid of 'Micmac'×'Bounty'. The pollen parent of 'Cavendish' was 'Annapolis', from 'K74-5'×'Earliglow'. The parentage of 'K74-5' was 'Micmac'×'Raritan'. 'Glooscap' is a high yielding, winter hardy cultivar released from the Agriculture Canada, Kentville breeding program in 1983. 'Annapolis', released in 1984, is an early maturing Kentville cultivar, that is resistant to red stele root rot. Seedlings of the cross were screened for red stele resistance using the sand bench method of Scott et al. (1976, Supra) with six isolates of race A-6 as inoculum. Symptomless plants were moved to a field infested with *P. fragariae* located at Robinsons Corner, Lunenburg Co., N.S. in the spring of 1982. A. R. Jamieson made the discovery/selection in 1983 that came to be known as 'Cavendish'. At the time of his discovery/selection, Dr. Jamieson called over D. L. Craig and G. W. Bishop and informed them of his discovery/selection which was made in accordance with Dr. Jamieson having sole responsibility to make a decision on selection. The new variety was first asexually reproduced by runners in 1984 under Dr. Jamieson's supervision at the Kentville Research Station in Kentville, Nova Scotia, Canada. Since 1987, propagules of the new variety have been tested at the Agriculture and Agri-Food Canada research centers in Kentville, Nova Scotia; Charlottetown, Prince Edward Island; and Fredricton, New Brunswick—all of Canada, and the variety has been found to retain its distinctive structure through successive propagation. 'Cavendish' has been stable and no off-types have been observed.

DESCRIPTION OF THE INVENTION

Figure 4:
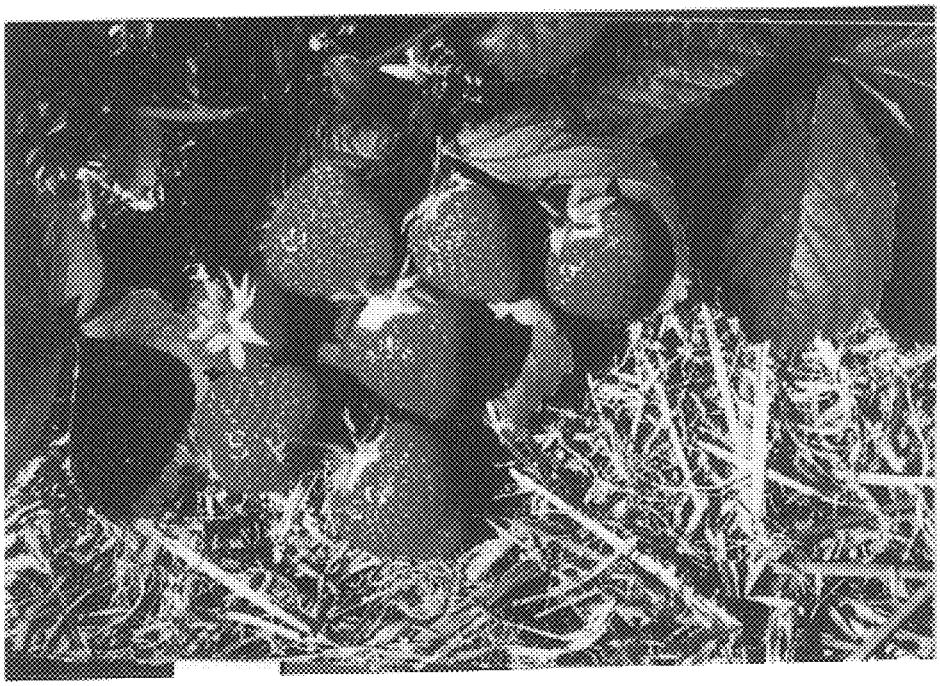
FIG. 4 shows 'Cavendish' fruit and leaves of the 'Cavendish' plant.

'Cavendish' plants are moderately vigorous, runnering well under good growing conditions but not excessively. The vigor of 'Cavendish' is rated as medium compared to strong for 'Honeoye' and 'Kent'. Crown size is small to medium. 'Cavendish' leaves emerge from the crown in the same way and at the same time as for 'Honeoye' and 'Kent'. 'Cavendish' plants are smaller and canopy density is less than for 'Honeoye' and 'Kent'. Leaves (FIG. 4) are trifoliolate and pinnate: the central leaflet is roundish-ovate with a slightly attenuated leaflet base, the side leaflets are oblique. Leaflet color is medium green on the upper surface and light waxy green on the lower surface. Leaflets commonly cup upwards at the margins exposing the lower surface and giving the foliage a light green appearance. Mean terminal leaflet through (mm) was found to be 79.9 for 'Cavendish' compared to 83.8 for 'Honeoye' and 82.5 for 'Kent'. Terminal leaflet length (mm) was found to range 64 to 89 for 'Cavendish' compared to 65 to 97 for 'Honeoye' and 72 to 100 for 'Kent'. The mean terminal leaflet width (mm) was found to be 74.6 for 'Cavendish' compared to 70.3 for 'Honeoye' and 72.3 for 'Kent'. Terminal leaflet width (mm) was found to range from 55 to 90 for 'Cavendish' compared to 55 to 87 for 'Honeoye' and 60 to 87 for 'Kent'. The terminal leaflet length/width ratio of mean values was found to be 1.07 for 'Cavendish' compare to 1.19 for 'Honeoye' and 1.14 for 'Kent'. The leaflets of 'Cavendish' are less elongated than those of 'Honeoye' and 'Kent'. Leaf blade serrations (21–28 leaflet) are moderately shallow and moderately blunt. Leaf petioles are of medium length with moderately numerous lateral to weakly descending hairs. Petiole bracts are absent from 'Cavendish'.

Figure 1:
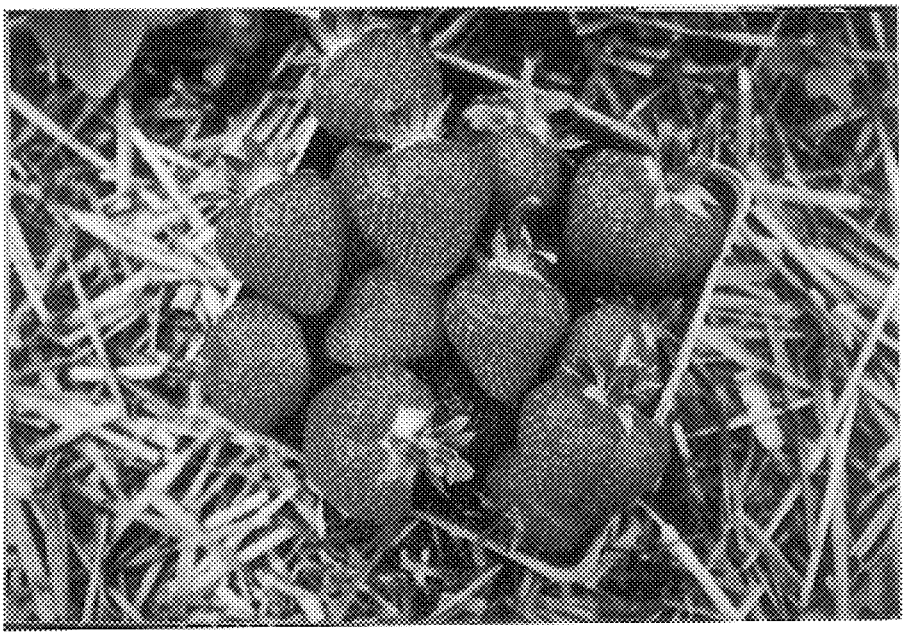
FIG. 1 shows the fruit of 'Cavendish'.
Figure 2:
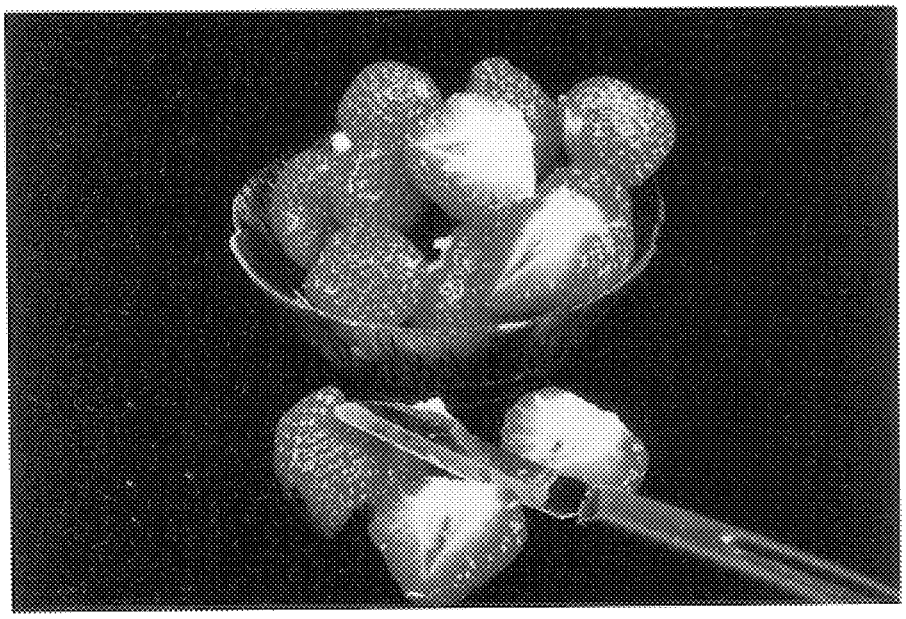
FIG. 2 shows the interior of the fruit of 'Cavendish'.
Figure 3:
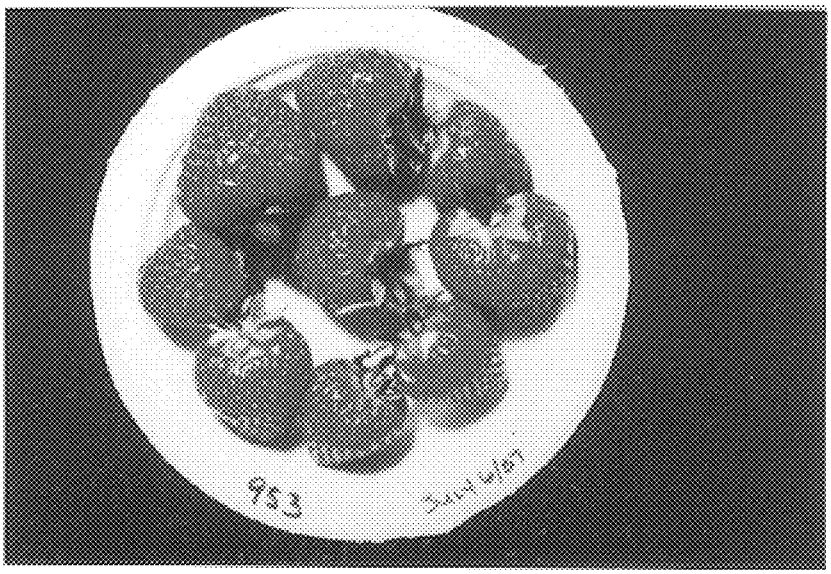
FIG. 3 shows 'Cavendish' fruit with calyx attached, on a plate, and the orientation of some of the fruit is such that whiteness under the calyx is evident.

'Cavendish' is typically grown in the matted row system in which it is planted in the spring of year one and produces flowers and fruit in following years, as are 'Honeoye' and 'Kent'. 'Cavendish' begins to flower after 'Honeoye' and before 'Kent'. 'Cavendish' begins to flower at or near June 2 at Kentville, Nova Scotia, Canada. Mean stalk length (cm) of flower stalks was found to be 20.4 for 'Cavendish' compared to 21.8 for 'Honeoye' and 29.8 for 'Kent'. Flower stalk (cm) length was found to range from 15 to 24 for 'Cavendish' compared to 19 to 24 for 'Honeoye' and 24 to 36 for 'Kent'. The flower stalk length for 'Cavendish' is similar to that for 'Honeoye' and shorter than that of 'Kent'. 'Cavendish' flowers beneath the canopy whereas 'Honeoye' flowers open level with the canopy and 'Kent' flowers above the canopy. 'Cavendish' and 'Kent' flowers are medium in size and 'Honeoye' flowers are medium-large. The diameter of the calyx is the same size as the diameter of the corolla for 'Cavendish' but for 'Honeoye' and 'Kent', the diameter of the calyx is smaller than the diameter of the corolla. The diameter of the inner calyx is the same as the diameter of the outer calyx for all three varieties. The petals of 'Cavendish' are slightly broader (12 mm) than long (11 mm) while the petals of 'Honeoye' and 'Kent' are as long as broad. Petals of all three varieties are white. Primary flowers of 'Cavendish' generally have 6 to 8 petals while secondary flowers have 5 to 6 petals. The sepal number is twice the number of the petals; primary flowers have 12 to 16 sepals while secondary and later flowers have 10 or 12 sepals. All three varieties have perfect flowers. However, the stamens are less well developed on 'Cavendish' than an 'Honeoye' and 'Kent'. The stamens on 'Cavendish' produce less pollen than do the stamens on 'Honeoye'. 'Kent' is intermediate in pollen production. In general, colors are: petals, white; sepals, mid-green; anthers, yellow; filaments, yellow-green; stigmas, yellow-green; styles, light yellow-green. Primary fruit are large, cordate in shape and slightly irregular (FIG. 1), beginning to ripen between 'Honeoye' and 'Kent'. The primary berries of 'Cavendish' range from 25 to 45 g. Secondary and later ripening berries are medium in size and short conic to conic in shape. Fruit shape of secondary berries for 'Cavendish' was similar to fruit shape of secondary berries for 'Honeoye' while the fruit shape of secondary berries for 'Kent' was broader. Mean fruit length (mm) for 'Cavendish' was found to be 31.8 compared to 29.91 for 'Honeoye' and 27.7 for 'Kent'. Fruit length (mm) was found to range from 28 to 35 for 'Cavendish' compared to 27 to 33 for 'Honeoye' and 25 to 30 for 'Kent'. Mean fruit width (mm) was found to be 34.6 for 'Cavendish' compared to 30.7 for 'Honeoye' and 36.3 for 'Kent'. Fruit width (mm) was found to range from 29 to 39 for 'Cavendish' compared to 27 to 34 for 'Honeoye' and 31 to 40 for 'Kent'. Fruit length/width ratio of mean values was found to be 0.92 for 'Cavendish' compared to 0.97 for 'Honeoye' and 0.76 for 'Kent'. 'Cavendish fruit were found to have a seasonal means of 15 g compared to 10 g for 'Honeoye' and 12 g for 'Kent'. Fruit surface color is deep red except under the calyx where it is white (FIG. 3). The white coloration of the flesh beneath the calyx distinguishes 'Cavendish' from 'Honeoye' and 'Kent'; however, there are a few other varieties (e.g., 'Blomidon') which share this trait. Fruit glossiness is tempered somewhat by a minute pubescence. Internal color fades from red near the skin to white just beneath the calyx at the core (FIG. 2). 'Cavendish' flesh is firm and skin is medium firm. The calyx is moderately reflexed at maturity and calyx removal (capping or hulling) is moderately difficult. The seed on fruit of 'Cavendish' and 'Honeoye' is indented from the fruit surface, while for 'Kent', the seed is even with the fruit surface. The seeds of all three varieties are ovate with one side flattened. Seeds of 'Cavendish' are the same size as those of 'Honeoye' (0.0005 g/seed) whereas those of 'Kent' are larger (0.0007 g/seed).

Performance

'Cavendish' consistently yielded higher than 'Redcoat' and 'Annapolis' (Table 1). 'Cavendish' equalled the yield of 'Kent' at Fredericton in 1988. The seasonal fruit weight of 'Cavendish' exceeded all other cultivars at Kentville (Table 1). As an estimate of primary fruit size, fruit weights were averaged at Kentville over the first two harvest dates in 1988 and 1989. 'Cavendish' primary fruits averaged 25.1 g compared to 'Kent' at 17.0 g.

TABLE 1

Fruit production of 'Cavendish' and three standard cultivars, averaged over two harvest seasons (1988 and 1989), in plots established in 1987 at Kentville, Nova Scotia and Fredericton, New Brunswick

| Cultivar | Total yield ($t\ ha^{-1}$) | Unmarketable (%) | Seasonal fruit weight (g) |
|---|---|---|---|
| | Kentville | | |
| Kent | 31.7 | 4.4 | 11.1 |
| Cavendish | 27.8 | 4.6 | 15.5 |
| Redcoat | 21.8 | 4.2 | 8.9 |
| Annapolis | 21.3 | 3.1 | 11.3 |
| Significance | *** | * | *** |
| SEM (n = 4, df = 24)[z] | 0.91 | 0.39 | 0.35 |
| | Fredericton | | |
| Kent | 24.1 | 9.9 | 18.4 |

TABLE 1-continued

Fruit production of 'Cavendish' and three standard cultivars, averaged over two harvest seasons (1988 and 1989), in plots established in 1987 at Kentville, Nova Scotia and Fredericton, New Brunswick

| Cultivar | Total yield (t $ha^{-1}$) | Unmarketable (%) | Seasonal fruit weight (g) |
|---|---|---|---|
| Cavendish | 20.8 | 4.9 | 19.8 |
| Redcoat | 16.3 | 4.7 | 14.9 |
| Annapolis | 15.9 | 1.1 | 19.7 |
| Significance | * | *** | *** |
| SEM (n = 3, df = 14)[z] | 1.58 | 0.87 | 0.38 |

[z]Degrees of freedom for the standard error of the mean (SEM) reflect a total number of clones of 8 at Kentville and 7 at Fredericton. Plots were 55 cm wide matted rows developed from an initial 60 cm in-row plant spacing. Plots at Kentville were 6.0 m long with 4 replications and plots at Fredericton were 4.2 m long with 3 replications.
***, *Significant difference at P < 0.001, and P < 0.05, respectively.

Disease Response

The response of 'Cavendish' to Verticillium wilt (*V. dahliae* Kleb.) has been evaluated in the greenhouse with methods similar to Galletta et al. (*Adv. Strawberry Prod.* 1:21, 1982). One isolate, obtained from a diseased 'Micmac' plant, was used as inoculum. 'Cavendish', 'Annapolis', 'Cornwallis', and 'Veestar' proved more resistant than 'Glooscap', 'Micmac', 'Kent', 'Honeoye', and 'Bounty'. 'Cavendish' was rated as resistant by the criteria of Galletta et al. (1982, Supra). however, in the field, plants with *Verticillium wilt* have been observed.

'Cavendish' is highly resistant to *P. fragaraie* races A-4, A-6, and A-7, the three races known to occur in commercial strawberry fields in Nova Scotia (Nickerson, unpublished). Resistance to red stele has been effective in grower trials on soils heavily infested with *P. fragariae.*

Fruit rot, principally caused by *Botrytis cinerea* Pers. ex Fr., is the primary cause for categorizing fruit as unmarketable in our trials. The proportion of the total yield of 'Cavendish', 'Kent', and 'Redcoat' considered unmarketable ranged from 2 to 7 percent over two years with no consistent cultivar differences. The incidence of postharvest fruit rot was recorded after 3 days incubation of fruit at 20 C and high relative humidity. 'Cavendish' has consistently produced fewer fruit with postharvest fruit rot than 'Kent' (Jamieson and Nickerson, *Acta Hort.* 265:85–90, 1989). In addition, the extent of colonization was less than on 'Kent'.

'Cavendish' shows an intermediate reaction to powdery mildew (*Sphaerotheca macularis* (Walls. ex Fr.) Jacz.) on the foliage. This level of resistance is higher than 'Annapolis' but lower than 'Kent'. Powdery mildew has not been observed on the fruit.

Virus diseases of strawberries are uncommon in Atlantic Canada and the virus tolerance of 'Cavendish' is unknown. 'Cavendish' is highly susceptible to green petal disease, as is its seed parent 'Glooscap'.

Fresh Fruit Evaluation

The fruit of 'Cavendish' was compared with that of 'Honeoye', 'Annapolis' and 'Kent'. Three methods of assessment were used to measure the quality of the cultivars:

1. A trained sensory panel rated the intensity of color, appearance, flavor and texture attributes. Methods used for the selection and training of panelists along with attribute definitions and reference material was previously reported by Sanford et al. (*Tech. Mem. No.* 89-02, *Food Res.*, Agric. Canada Res. Sta. Kentville N.S., 1989). All experimental conditions including sample preparation, presentation and experimental design were similar to those described by Sanford and Jamieson (*Tech. Mem. No.* 89-03, *Food Res.*, Agri. Canada Res. Sta. Kentville, N.S, 1989) where for each grouping of 4 cultivars, both harvest and panelist were treated as blocks. Harvest, panelist and cultivar effects were estimated through an analysis of variance for each sensory attribute.

2. Selected instrumental measurements were made. At each harvest, firmness of 10 berries of each cultivar was measured using a notched head probe attached to an Accuforce II model AF-100 digital force gauge (Ametek, Hunter Spring Division, Hatfield, Pa.). Twice at each harvest soluble solids of juice expressed from the fruit was measured using a refractometer and total acidity was measured by titrating a 50 mL sample with 0.5N NaOH to pH 8.1 with a Mettler DL40RC automatic titrator (Mettler Instruments AG, Zurich, Switzerland).

3. An acceptance test was conducted with a panel composed of 56 staff members rating each cultivar for overall acceptability at each of two harvests in 1989. Histograms describing the distributions of the responses in each category of the 8-point scale were produced for each cultivar. After determining that the distributions were unimodal, the cultivar effects were estimated in a regression using a general linear model for the normal distribution.

TABLE 2

Taste panel evaluation of flavor components and instrumental measurements of soluble solids and acidity of 'Cavendish' and three other strawberry cultivars grown at Kentville, Nova Scotia.

| | Flavor Component Ratings[z] | | | | | |
|---|---|---|---|---|---|---|
| Cultivar | Aroma | Sweet | Tart | Flavor strength | Melon-like | Honey-like |
| Cavendish | 7.2 | 7.1 | 6.0 | 6.4 | 4.7 | 2.8 |
| Honeoye | 8.3 | 5.7 | 7.8 | 6.6 | 3.9 | 2.4 |
| Annapolis | 7.3 | 6.7 | 6.6 | 6.8 | 3.0 | 2.5 |
| Kent | 4.7 | 6.0 | 6.3 | 4.7 | 3.4 | 2.2 |
| Signif. | *** | *[y] | * | ** | *[x] | NS |
| SEM | 0.44 | 0.38 | 0.47 | 0.47 | 0.42 | 0.30 |
| | | | (n = 40, df = 60) | | | |

| | Flavor Component Ratings[a] | | | Instrumental Measurements: Soluble solids | Instrumental Measurements: Titratable acids |
|---|---|---|---|---|---|
| Cultivar | Musty | Bitter | Astringent | (%) | (mg/100 mL) |
| Cavendish | 3.3 | 4.2 | 5.9 | 8.1 | 0.84 |
| Honeoye | 3.4 | 5.2 | 7.4 | 8.2 | 1.14 |
| Annapolis | 3.9 | 4.3 | 5.4 | 8.8 | 1.00 |
| Kent | 2.6 | 3.4 | 4.9 | 7.9 | 0.93 |
| Signif. | NS | NS | * | NS | ** |
| SEM | 0.57 | 0.53 | 0.54 | 0.29 | 0.042 |
| | | | | (n = 8, df = 7) | |

[z]Mean values of 40 ratings (10 panelists × 2 harvests × 2 years). Ratings were on a scale of 0–15 representing weak–strong (aroma, falvor strength, melon-like, honey-like, and mustiness) and slightly–extremely (sweetness, tartness, bitterness, and astrigency).
[y]A significant (P < .05) harvest by variety interaction indicated that 'Annapolis' was rated more sweet at the second harvest.
[x]A significant (P < .05) harvest by variety interaction indicated that 'Honeoye' was rated more intense in melon-like flavor at the first harvest.
*, , *, NS significant at P < .001, P < .01, P < .05, not significant, respectively.

The sensory panel described 'Cavendish' as having a similar intensity of berry aroma and flavor as 'Honeoye', and 'Annapolis' but significantly stronger aroma and flavor than 'Kent' (Table 2). The cultivars did not vary in level of mustiness or honey-like flavor, but 'Cavendish' had a stronger melon-like flavor. 'Cavendish' was described as significantly sweeter and less tart than 'Honeoye'. While soluble solids were not significantly different among the cultivars, the titratable acid levels were comparable with the sensory data with 'Cavendish' being less acid than 'Honeoye' (Table 2). The lower acid level may have also resulted in the berries being perceived as sweeter than 'Honeoye' even though the soluble solids levels were similar. 'Cavendish' fruit was described by the trained sensory panel as dark red and glossy, similar in depth of color to 'Honeoye' and in glossiness to 'Kent' (Table 3). According to both the sensory and instrumental measurements (Table 3), the firmness of 'Cavendish' and 'Honeoye' were similar. Also, the two cultivars received comparable ratings for pulpiness. Like 'Annapolis', the fruit of 'Cavendish' was very juicy.

'Cavendish' received higher acceptance ratings than 'Honeoye' and 'Annapolis' (Table 3). Panelists rated 'Cavendish', 'Kent', 'Annapolis' and 'Honeoye' as acceptable (rating scale categories 5–8) in 76, 73, 66, and 56%, respectively, of the acceptance tests.

TABLE 3

Taste panel evaluation of appearance and texture, instrumental measurement of firmness, and consumer acceptance of 'Cavendish' and three other strawberry cultivars grown at Kentville, Nova Scotia.

| | Appearance | | Texture[z] | | | Firmness | Accep- |
|---|---|---|---|---|---|---|---|
| Cultivar | Color | Gloss | Firm | Juicy | Pulpy | (N) | tance[y] |
| Cavendish | 11.1 | 9.2 | 5.5 | 10.1 | 4.6 | 4.0 | 5.6 |
| Honeoye | 10.5 | 6.7 | 5.4 | 8.9 | 4.7 | 3.8 | 4.5 |
| Annapolis | 7.1 | 7.7 | 4.0 | 10.6 | 3.5 | 3.7 | 4.9 |
| Kent | 6.7 | 10.0 | 6.7 | 8.9 | 6.1 | 4.8 | 5.2 |
| Significance | *** | *** | ** | ** | ** | NS | ** |
| SEM | 0.51 | 0.47 | 0.45 | 0.51 | 0.47 | 0.33 | 0.22 |
| | (n = 40, df = 60) | | | | | (n = 40, df = 7) | (n = 112, df = 11) |

[z]Mean values of 40 ratings (10 panelists × 2 harvests × 2 years). Ratings were on a scale of 0–15 representing light red–dark red (color), flat–glossy (gloss), soft–firm (firmness), dry–juicy (juiciness), and none–extremely (pulpiness)
[y]Mean values for overall acceptance (1 = extremelyunacceptable, 8 = extremely acceptable) as measured at each of two harvests in 1989 by 1 56-member panel. As part of a larger, uinbalanced experiment, these 4 cultivars were compared with 8 other cultivars.
*, , NS significant at $P < .001$, $P < .01$, not significant, respectively.

As reported in Table 3, the cultivar 'Cavendish' received a color rating of 11.2 (dark red) on a 0–15 scale. This scale was referenced to the Munsell color system (Munsell Book of colors, MacBeth, Kollmorgen Corp., Baltimore, Md.).

The following Munsell color chips were used as scale reference points:

| SCALE POINT | DESCRIPTION | MUNSELL COLOR CHIP |
|---|---|---|
| 1.5 | Light Red | 7.5R 4/12 |
| 7.5 | Medium Red | 7.5R 3/10 |
| 13.5 | Dark Red | 7.5R 2/8 |

Munsell colors are described in terms of three attributes: hue, value and chroma. Hue describes the color by name (e.g. red), while value indicates lightness or darkness of color and chroma indicates the degree of departure of a given hue from a neutral gray of the same value.

Munsell color determined for the crowns of dormant runners was 2.5GY 9/2 for 'Cavendish', 'Honeoye' and 'Kent'. 'Cavendish' had a short crown, and 'Honeoye' and 'Kent' had long crowns.

The Munsell color for petiole on the lower one inch of petiole attached to a dormant crown was determined to be 5GY 7/6 for 'Cavendish', 2.5GY 7/4 for 'Honeoye', and 5GY 6/6 for 'Kent'.

The Munsell color of the yellow ground color of seed of the three varieties was the same 7.5Y 8/6 and of the red over-color of the three varieties was the same 5R 4/8. Fifteen percent of 'Cavendish' seed were found to have over-color compared to 30 percent for 'Honeoye' and 40 percent for 'Kent'.

The colors of the leaves, calyx, and petals are typical of the species and market class.

The color of 'Cavendish' fruit was also determined on a D25-L Hunterlab Tristimulus Colorimeter (Hunter Associates, Reston, Va.). The Hunterlab instrument gives color measurements in the Hunter L, a, and b, opponent color scales. The dimension 'L' gives a measure of lightness and ranges from 0 for black to 100 for perfect white. When positive, the 'a' value gives a measure of 'redness' and when negative the amount of 'greenness' is estimated. A positive Hunter 'b' value gives a measure of 'yellowness' while a negative 'b' gives a rating of the 'blueness'. For both the 'a' and 'b' values, a scale value of 0 is grey. Together the three values (L, 'a' and b) describe the strawberry in terms of the perceptual attributes of color—lightness, hue and saturation. Lightness indicates how 'light' or 'dark' the color is, while hue describes the actual color by name e.g. red. green, yellow. by describing how much the sample is colored as opposed to achromatic, saturation characterizes the vividness or dullness of color.

The Hunterlab values for 'Cavendish' averaged over two years and with two harvests per year were:

L=19.0 a=+21.4 b=+7.6

Hue=19.3

Saturation=22.7

Harvest

The pedicels of picked primary fruit are short (0.5–2 cm), thick, curved and pubescent, and primary berries are difficult to pick. The peduncles of picked secondary berries are short (1–3 cm), medium in thickness, slightly curved and pubescent, and secondary berries are easy to pick. 'Cavendish' is more difficult to harvest than 'Honeoye' and 'Kent' because of a great force needed to break the pedicels of the primary fruit. The removal of calyx from the berry is difficult for 'Cavendish' and 'Kent' but easier for 'Honeoye'. 'Cavendish' is not adapted for mechanical harvest. At Kentville, Nova Scotia, the harvest for 'Cavendish' is in the early mid-season, and has been observed to begin on June 28 and end on July 24 and to last for about four weeks.

Planting

Runner plants are typically dug in November, and in Nova Scotia have received significant chilling in the nursery field. In addition, they are typically stored at minus 2° C. for five or six months until planting in the spring. Alternatively, plants are dug in the spring after a full winter of chilling in the field. 'Cavendish' responds like other northern varieties; no special pre-planting treatment is required. We do not know how 'Cavendish' would respond to southern conditions.

Genetic Fingerprinting

Random amplified polymorphic DNA (RAPD) patterns were determined for 'Cavendish' and six other strawberry varieties using primers UBC59, UBC76, UBC85, UBC100, and UBC287 in testing done in the Biotechnology Lab of the Atlantic Food and Horticultural Research Centre following the techniques of Levi, et al., "Identification of Strawberry Genotypes and Evaluation of their Genetic Relationships Using Randomly Amplified Polymorphic DNA (RAPD) Analysis," Advances in Strawberry Research, 13, 36–39 (1994). The results are set forth in Table 4, below, where bands from reliable polymorphic RAPD fragments from three replications are represented as 0 equal to absent or 1 equal to present.

TABLE 4

| | PRIMER | | | | |
|---|---|---|---|---|---|
| | UBC59 | UBC76 | UBC85 | UBC100 | UBC287 |
| | Band Number for each primer and DNA pattern | | | | |
| Variety | 12345 | 123 | 123 | 12345 | 123 |
| 'Cavendish' | 11011 a | 101 c | 000 a | 11100 a | 111 d |
| 'Scott' | 10010 b | 100 a | 100 b | 0010 b | 010 a |

TABLE 4-continued

| | PRIMER | | | | |
|---|---|---|---|---|---|
| | UBC59 | UBC76 | UBC85 | UBC100 | UBC287 |
| | Band Number for each primer and DNA pattern | | | | |
| Variety | 12345 | 123 | 123 | 12345 | 123 |
| 'Honeoye' | 10011 c | 000 b | 010 c | 10100 c | 011 b |
| 'Totem' | 10001 d | 100 a | 000 a | 11110 d | 101 c |
| 'Annapolis' | 01111 t | 101 c | 010 c | 11101 e | 011 b |
| 'Blomidon' | 11111 f | 101 c | 010 c | 11010 g | 011 b |
| 'Kent' | 11111 f | 100 a | 011 e | 10110 h | 011 b |

In each vertical column in Table 4, identical letters identify identical patterns.

Primers UBC59, UBC100 and UBC287 provided banding patterns for 'Cavendish' distinct from the banding patterns of the other varieties. The primer UBC100 produced a distinct pattern for each of the seven varieties.

Adaptability and Use

'Cavendish' appears to be well adapted throughout the Atlantic provinces of Canada, when green petal disease is managed. Wider suitability to Northeastern U.S.A. and Quebec is likely, based on parental performance. 'Cavendish' will be of particular value on soils infested with *P. fragariae*, providing a high yielding cultivar following 'Annapolis' in ripening. The fruit should meet the fresh market requirements for pick-your-own and short distance shipping.

We claim:

1. The new and distinct variety of strawberry plant herein described and illustrated and identified by the characteristics enumerated above.

* * * * *

UNITED STATES PATENT AND TRADEMARK OFFICE

CERTIFICATE OF CORRECTION

PATENT NO. : Plant 11,110

DATED : October 26, 1999

INVENTOR(S) : Andrew R. Jamieson

It is certified that error appears in the above-identified patent and that said Letters Patent is hereby corrected as shown below:

On the title page, change [75] to delete Nickerson and Sanford as inventors so [75] is --Inventors: Andrew R. Jamieson, Kentville, Canada--.

Signed and Sealed this

Twentieth Day of June, 2000

*Attest:*

Q. TODD DICKINSON

*Attesting Officer*

*Director of Patents and Trademarks*